(12) United States Patent
Efimov

(10) Patent No.: US 10,422,868 B2
(45) Date of Patent: Sep. 24, 2019

(54) OPTICAL HETERODYNE DETECTION OF AIR PRESSURE, TEMPERATURE, AND WIND VELOCITY AND METHOD

(71) Applicant: HRL Laboratories, LLC, Malibu, CA (US)

(72) Inventor: Oleg M. Efimov, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 108 days.

(21) Appl. No.: 15/648,274

(22) Filed: Jul. 12, 2017

(65) Prior Publication Data

US 2018/0172809 A1    Jun. 21, 2018

Related U.S. Application Data

(60) Provisional application No. 62/453,468, filed on Feb. 1, 2017.

(51) Int. Cl.
*G01S 7/491* (2006.01)
*G01P 13/04* (2006.01)
(Continued)

(52) U.S. Cl.
CPC ............ *G01S 7/4917* (2013.01); *G01K 11/32* (2013.01); *G01N 21/47* (2013.01); *G01N 21/63* (2013.01); *G01P 13/045* (2013.01); *G01R 31/2829* (2013.01); *G01S 7/4802* (2013.01); *G01S 7/4811* (2013.01); *G01S 7/4818* (2013.01); *G01S 17/325* (2013.01); *G01S 17/58* (2013.01); *G01S 17/95* (2013.01); *H04L 27/103* (2013.01); *H04L 27/144* (2013.01); *G01K 2011/322* (2013.01); *G01R 35/005* (2013.01); *Y02A 90/19* (2018.01)

(58) Field of Classification Search
CPC ...... G01N 21/47; G01N 21/63; G01S 7/4917; G01S 7/4802; G01S 7/4814; G01S 7/4818; G01S 17/325; G01S 17/95; G01P 13/045; G01P 5/26
See application file for complete search history.

(56) References Cited

U.S. PATENT DOCUMENTS

| 7,106,447 B2 | 9/2006 | Hays |
| 7,508,528 B2 | 3/2009 | Hays et al. |

(Continued)

OTHER PUBLICATIONS

From PCT/US2017/041774, International Search Report and Written Opinion dated Oct. 31, 2017.
(Continued)

*Primary Examiner* — Bryan Bui
(74) *Attorney, Agent, or Firm* — Ladas & Parry

(57) ABSTRACT

An apparatus for measuring at least one of pressure, temperature, and wind velocity of a volume of air includes a laser having a first frequency and a second frequency of radiation, a first waveguide coupled to the laser, a second waveguide, a narrowband filter coupled between the first waveguide and the second waveguide, wherein the narrowband filter is configured to redirect the first frequency to the second waveguide, and a photodetector coupled to the second waveguide, wherein the first frequency is transmitted by the first waveguide to the volume of air, scattered light is received from the volume of air, and the photodetector mixes the first frequency on the second waveguide with the received scattered light.

25 Claims, 4 Drawing Sheets

(51) Int. Cl.
| | |
|---|---|
| G01S 7/481 | (2006.01) |
| G01S 17/32 | (2006.01) |
| G01S 17/58 | (2006.01) |
| G01S 17/95 | (2006.01) |
| G01S 7/48 | (2006.01) |
| G01N 21/47 | (2006.01) |
| G01N 21/63 | (2006.01) |
| G01R 31/28 | (2006.01) |
| H04L 27/10 | (2006.01) |
| H04L 27/144 | (2006.01) |
| G01K 11/32 | (2006.01) |
| G01R 35/00 | (2006.01) |

(56) References Cited

U.S. PATENT DOCUMENTS

| | | | |
|---|---|---|---|
| 7,820,970 B1* | 10/2010 | Shaw | G01J 5/08 |
| | | | 250/338.1 |
| 8,908,160 B2 | 12/2014 | Dakin et al. | |
| 9,606,234 B2* | 3/2017 | Major, Jr. | G01S 7/4811 |
| 2004/0233458 A1 | 11/2004 | Frick | |
| 2013/0162974 A1 | 6/2013 | Dakin et al. | |
| 2013/0258342 A1 | 10/2013 | Schnier | |
| 2014/0036252 A1 | 2/2014 | Amzajerdian et al. | |

OTHER PUBLICATIONS

Cezard, et al., "Performance evaluation of a dual fringe-imaging Michelson interferometer for air parameter measurements with a 355nm Rayleigh—Mie lidar," Applied Optics vol. 48, No. 12, pp. 2321-2332 (Apr. 20, 2009).

Derickson, "Fiber optic test and measurement," Prentice-Hall, Section 5.2.2, pp. 175-179 (1998).

Fraczek et al., "Short-range optical air data measurements for aircraft control using rotational Raman backscatter," Optics Express, vol. 21, No. 14, pp. 16398-16414 (Jul. 15, 2013).

Gao et al., "Frequency-modulated continuous-wave lidar using I/Q modulator for simplified heterodyne detection," Opt. Lett., v. 37, No. 11, p. 2022 (2012).

Hryniewicz, et al., "Higher Order Filter Response in Coupled Microring Resonators," IEEE J. Photonics Technology Letters, v. 12, No. 3, p. 320 (2000).

Karlsson et al., "Linearization of the frequency sweep of a frequency-modulated continuous-wave semiconductor laser radar and the resulting ranging performance," Appl. Opt., v. 38, No. 15, p. 3376 (1999).

Karlsson, et al., "All-fiber multifunction continuous-wave coherent laser radar at 1.55 mm for range, speed, vibration, and wind measurements," Appl. Opt., v. 39, No. 21, p. 3716 (2000).

Little, et al., "Microring resonator channel dropping filters," J. Lightwave Technology, v. 15, No. 6, p. 998 (1997).

Tenti et al., "On the kinetic model description of Rayleigh-Brillouin scattering from molecular gases," Canadian Journal of Physics, vol. 52, pp. 285-290 (1974).

Witschas, "Analytical model for Rayleigh—Brillouin line shapes in air," Applied Optics, vol. 50, No. 3, pp. 267-270 (Jan. 20, 2011).

From U.S. Appl. No. 15/609,788 (unpublished), Application and Office Actions.

U.S. Appl. No. 15/609,788, Efimov, filed May 31, 2017.

From PCT/US2017/041774, International Preliminary Report on Patentability (IPRP; Ch. II) dated Dec. 17, 2018.

* cited by examiner

OPTICAL HETERODYNE DETECTION OF AIR PRESSURE, TEMPERATURE, AND WIND VELOCITY AND METHOD

CROSS REFERENCE TO RELATED APPLICATIONS

This application relates to U.S. patent application Ser. No. 15/609,788 filed May 31, 2017, and U.S. Provisional Patent Application 62/450,047, filed Jan. 24, 2017, and relates to and claims the benefit of priority from U.S. Provisional Patent Application 62/453,468, filed Feb. 1, 2017, which are incorporated herein by reference as though set forth in full.

TECHNICAL FIELD

This disclosure relates to techniques for measuring air pressure, air temperature, and wind velocity.

BACKGROUND

Determination of air pressure, air temperature, and wind velocity is very important for reliable control of flight. The measurement of scattered light parameters in air is a relatively new optical remote-sensing technique. Different high spectral resolution methods have been used in the prior art to make these measurements. Reference [2] below, which is incorporated herein by reference, describes using a Fabry-Perot interferometer to make the measurements. The air parameters are calculated by comparing the fringe parameters of reference and scattered beams. Reference [2] does not describe technical details about the measurements or their accuracy. For instance, the temperature of air is taught to be calculated directly from the fringe width associated with a spectral width of a Rayleigh-Brillouin scattering (RBS) line. This should result in considerable error because the spectral width depends both on temperature and pressure. The other disadvantages of the prior art Reference [2] method are its large physical size and a high sensitivity of a Fabry-Perrot interferometer to mechanical vibration.

A similar method has been described in Reference [3] below, which is incorporated herein by reference, for air parameter measurement using a dual fringe-imaging Michelson interferometer. The main disadvantages of the Reference [3] method include the need for a high power pulsed laser, a large physical size, and a high sensitivity of single and dual Michelson interferometers to mechanical vibration. The method used an approximation of the RBS line shape by a Gaussian profile, which resulted in considerable errors in the temperature and pressure measurements even for low atmospheric pressure when the spectral line had close to a Gaussian shape.

Short-range optical air data measurements using rotational Raman backscatter have been demonstrated in Reference [4] below, which is incorporated herein by reference. The main disadvantages of this method include the need for a high power pulsed laser, a large number of pulses (1000) needed for accurate data derivation resulting in a long time for the measurements, and the impossibility of wind velocity detection.

Heterodyne detection is a well-known method for high-resolution spectral measurements, as described in Reference [1] below, which is incorporated herein by reference. Reference [5] below, which is incorporated herein by reference, describes a method for measurement of air parameters based on heterodyne detection. However, Reference [5] only describes measuring wind velocity to be measured by this technique, which describes using fluorescent light intensity decay of some air molecules excited by radiation from special lasers. The techniques to measure the other parameters are not described in Reference [5].

The prior art does not describe using the spectra of RBS to accurately measure by heterodyne detection air pressure, air temperature, and wind velocity from the spectral line shape and the spectral line position.

The radiation of a narrowband laser may be split and used both for the exposure of an air volume to generate a scattered signal and for a reference beam for heterodyne detection of a multi-gigahertz RBS line. In this case the beat frequency produced by mixing of radiations on a photodetector should be displaced from 0 Hz by the multi-gigahertz frequency shift to accurately measure both the shape of the RBS line and the sign of Doppler shift for unambiguous measurement of wind velocity. This requires application of a high-frequency shifter. The prior art teaches frequency shifters using acousto-optic modulators which cannot provide the required large shift at any wavelength.

Another way for to provide heterodyne detection of a broad RBS line is to use two stable narrowband lasers with close frequencies. However, each laser has jitter and the frequency jitters of two different lasers causes a very noisy signal and the result is that the measurements have a low accuracy.

REFERENCES

The following references are incorporated herein by reference as though set forth in full.
[1] Prentice-Hall, 1998: "Fiber optic test and measurement," D Derickson editor, Section 5.2.2.
[2] P. Hays, "Molecular optical air data systems (MOADS)," U.S. Pat. No. 7,106,447 (2006).
[3] N. Cezard, et al., "Performance evaluation of a dual fringe-imaging Michelson interferometer for air parameter measurements with a 355 nm Rayleigh-Mie lidar," Appl. Opt., V. 48, No. 12, P. 2321, (2009).
[4] M. Fraczek, A. Behrendt, N. Schmitt, "Short-range optical air data measurements for aircraft control using rotational Raman backscatter," Opt. Express, v. 21, No. 14, P. 16398 (2013).
[5] E. A. Dakin, "Optical air data system suite for sensors," U.S. Pat. No. 8,908,160 (2014).
[6] G. Tenti, C. Boley, and R. Desai, "On the kinetic model description of Rayleigh-Brillouin scattering from molecular gases," Can. J. Phys. 52, 285-290 (1974).
[7] Witschas B, "Analytical model for Rayleigh-Brillouin line shapes in air," Appl. Opt., 50, 267-270 (2011).

What is needed is a method for measurement that has much lower noise and more accurate detection of the RBS spectral line to provide much better accuracy in the measurements of air pressure, air temperature, and wind velocity. The embodiments of the present disclosure answer these and other needs.

SUMMARY

In a first embodiment disclosed herein, an apparatus for measuring at least one of pressure, temperature, and wind velocity of a volume of air comprises a laser having a first frequency of radiation and a second frequency of radiation, a first waveguide coupled to the laser, a second waveguide, a narrowband filter coupled between the first waveguide and the second waveguide, wherein the narrowband filter is configured to redirect the first frequency to the second waveguide, and a photodetector coupled to the second waveguide, wherein the first frequency is transmitted by the first waveguide to the volume of air, wherein scattered light is received from the volume of air, and wherein the photodetector mixes the first frequency on the second waveguide with the received scattered light.

In another embodiment disclosed herein, a method of measuring at least one of air pressure, temperature, and wind velocity comprises transmitting a first frequency of radiation from a laser and a second frequency of radiation from the laser through a first waveguide, redirecting the first frequency of radiation into a second waveguide, transmitting the second frequency of radiation from first waveguide to a volume of air, receiving scattered light from the volume of air, mixing the received scattered light with the first frequency of radiation on a photodetector, measuring a spectrum of a beat frequency from photodetector, and deriving at least one of air pressure, air temperature, and wind velocity including wind direction from a measured spectrum of the received scattered light, wherein the received scattered light comprises Rayleigh-Brillouin scattering.

In yet another embodiment disclosed herein, an apparatus for measuring at least one of pressure, temperature, and wind velocity of a volume of air comprises a laser having a first frequency of radiation and a second frequency of radiation, a first waveguide coupled to the laser, a second waveguide, a narrowband filter coupled between the first waveguide and the second waveguide, wherein the narrowband filter is configured to redirect the first frequency to the second waveguide, at least one collimator coupled to the first waveguide, wherein the second frequency is transmitted by the at least one collimator to the volume of air, a first, a second, and a third photodetector, a second collimator coupled to the first photodetector by a third waveguide, a third collimator coupled to the second photodetector by a fourth waveguide, a fourth collimator coupled to the third photodetector by a fifth waveguide, wherein the second, third and fourth collimators are set in non-collinear directions, wherein scattered light from the volume of air is received by the second, third and fourth collimators, wherein the first photodetector is coupled to the second waveguide and mixes the first frequency with the received scattered light from the second collimator, wherein the second photodetector is coupled to the second waveguide and mixes the first frequency with the received scattered light from the third collimator, and wherein the third photodetector is coupled to the second waveguide and mixes the first frequency with the received scattered light from the fourth collimator.

These and other features and advantages will become further apparent from the detailed description and accompanying figures that follow. In the figures and description, numerals indicate the various features, like numerals referring to like features throughout both the drawings and the description.

DETAILED DESCRIPTION

Figure 1:
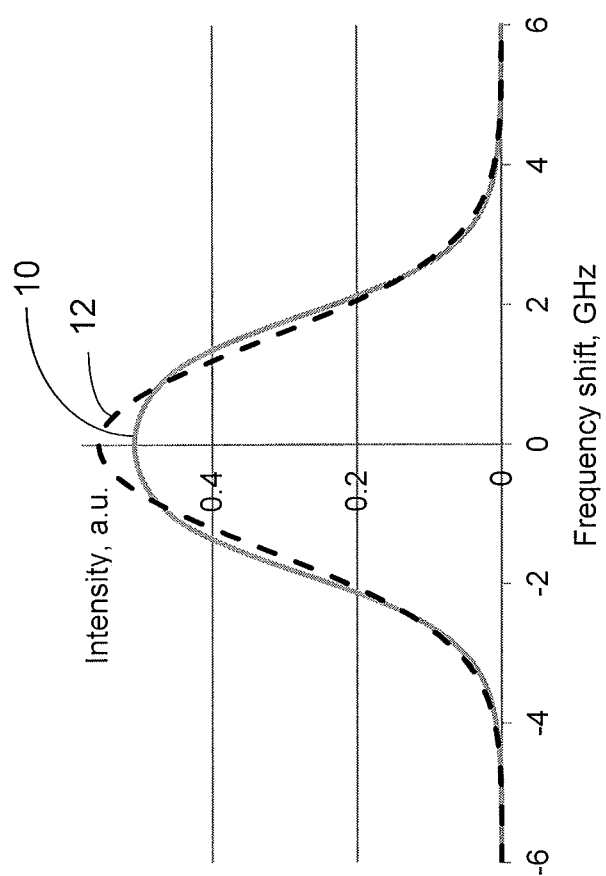
FIG. 1 shows a Rayleigh-Brillouin scattering (RBS) spectra of laser radiation at 405-nm wavelength at different atmospheric conditions.

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

As described above, the spontaneous Rayleigh-Brillouin scattering (RBS) of laser light by air can be used in atmospheric remote sensing to derive the pressure, temperature, and bulk velocity of the air by comparing the measured RBS spectrum with appropriate line shape models. The present disclosure describes an apparatus and a method for remote measurement of RBS line shape and its frequency displacement to calculate air pressure, air temperature, and wind velocity. Wind velocity includes the wind speed and its direction.

In the present disclosure a dual frequency laser is used. One of the frequencies of the laser is used as a reference beam and another frequency of the laser is transmitted as a signal beam to a definitive volume of air and is scattered and reflected from the volume of air. The reference beam and the received scattered signal beam are mixed on a photodetector (PD) for spectral measurement of beat frequency characteristics.

The method and apparatus of the present disclosure provide remote measurements of air pressure, air temperature, and wind velocity by detection of an RBS spectral line shape and spectral shift of the central frequency. Air data acquisition systems are needed for flight applications to provide parameters of air at different altitudes. In the prior art, separated devices are used to collect the above mentioned information: pitot tubes and thermistors are used for external pressure and temperature measurements correspondingly. In the prior art, accurate data about wind velocity at flight altitude is not available.

The main advantage of the presently disclosed method arises from application of the radiation of a dual frequency laser for heterodyne detection. The method provides large spectral displacement of heterodyne beat frequency from 0 Hz, which is needed for accurate measurement of a broadband line of RBS spectrum. The spectral displacement does not require electronic or electro-optic modulators. Another important advantage of the present method is that the utilization of two frequencies from the same laser for heterodyne detection provides unambiguous measurement of the direction of the wind velocity.

To summarize, the presently disclosed apparatus and method (1) provide a large spectral shift of beat frequency on a photodetector (PD) (2) make possible unambiguous measurement of wind velocity and its direction, (3) greatly reduce frequency jitter between the reference and signal frequencies, and (4) does not require application of additional electronic or electro-optic modulators. Therefore, an accurate measurement of a broad RBS line and a shift of its frequency can be made to reliably extract air data including directional wind velocity without any active means for heterodyne detection. An additional advantage of the present disclosure is that the progress in semiconductor lasers during the last decade allows the apparatus to have very small size and weight.

It is important to estimate the RBS line parameters to understand the requirements for the system needed for spectral measurement of the RBS line. Currently the Tenti S6 model, as described in Reference [6], which is incorporated herein by reference, is recognized as the best mathematical model to describe the spectral RBS line shape at different atmospheric conditions. However, the mathematical complexity of the Tenti S6 model makes it difficult to apply. In recent years, another analytical model for the RBS line shape in air has been proposed by Witschas, the G3 model, which is described in Reference [7], which is incorporated herein by reference. The G3 model can be used for very fast extraction of air data from measured RBS spectra with accuracies well below 1% up to an air pressure of 2 atm. A unit of air pressure (atm) may be defined as $1.01325*10^5$ N/m$^2$, and can also be stated as 1.01325 bar or 101325 pascal (Pa). Based on the G3 model, FIG. 1 shows simulations of RBS line shapes at different atmospheric pressures. Curve 10 on FIG. 1 shows the RBS spectra of laser radiation at a 405 nm wavelength, a pressure of 1.0 bar and a temperature of T=293° K. Curve 12 on FIG. 1 shows the RBS spectra of laser radiation at a 405 nm wavelength, a pressure of 0.1 bar and a temperature of T=293° K.

The amplitude, width, and shape of the RBS spectrum are dependent on both air pressure and its temperature, and the relationship can be mathematically described (see Reference [7]). Therefore, not only the amplitude and the spectral width of the RBS spectra should be measured but the complete RBS spectral shape should be fit for accurate derivation of air data from the measurements. The Doppler shift of frequency at speed of flight for a 405 nm wavelength laser radiation is close to 2 GHz, which means that the total value of displacement of the RBS line from 0 Hz should be more than 6 GHz for reliable heterodyne detection.

Figure 2:
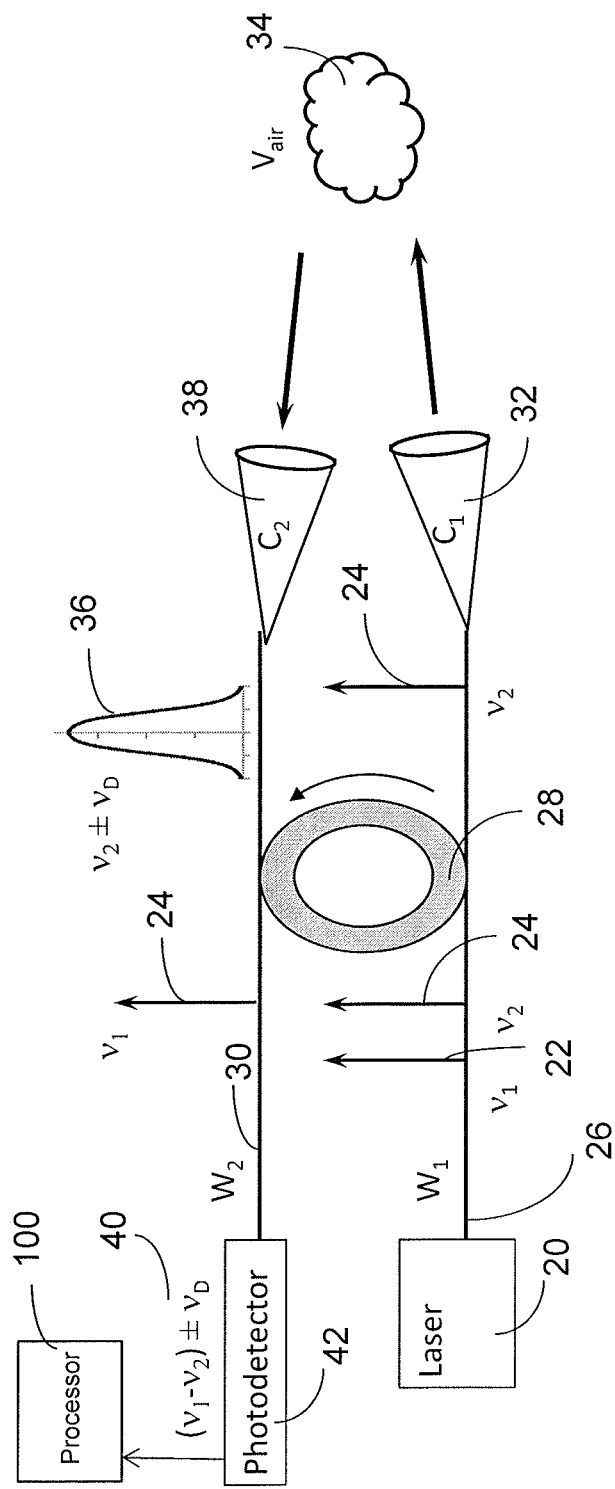
FIG. 2 shows an embodiment of an apparatus for measurement of at least one of air pressure, temperature, and wind velocity in accordance with the present disclosure.

Now referring to FIG. 2, radiation of laser 20 with frequencies of $v_1$ 22 and $v_2$ 24 is coupled to waveguide $W_1$ 26. Then the radiation of frequency $v_1$ 22 is coupled by optical microresonator 28, which is a narrow bandpass filter, and redirected into waveguide $W_2$ 30. The radiation of frequency $v_2$ 24 is transmitted past the filter 28, outcoupled from the waveguide $W_1$ 26 through collimator $C_1$ 32 and beamed to the definite air volume $V_{air}$ 34. The air volume 34 scatters and reflects the beam. A broadband spectral line of RBS of central frequency $v_2$ with Doppler shift $+v_D$ or $-v_D$ 36 is received by collimator $C_2$ 38 and coupled into waveguide $W_2$ 30. This spectral line is transmitted past the filter 28 without coupling and is mixed with the reference frequency $v_1$ 22 on photodetector (PD) 42 developing beat frequency $(v_1-v_2)\pm v_D$ 40. The apparatus of FIG. 2 provides not only a large shift of the beat frequency from 0 Hz but also allows measurement of the sign of the Doppler shift, which gives an unambiguous measurement of the direction of the wind velocity. The shift of the beat frequency from 0 Hz depends on the design of the laser 20 cavity, as is further discussed below.

An output of photodetector 42 may be connected to a processor 100 in order to derive the wind velocity including its direction, and also to derive the air temperature and air pressure.

It is known that frequency separation between any two adjacent laser modes is equal to c/(2nL), where c is the speed of light, n is the refractive index of the cavity material, and L is the cavity length. Therefore, any laser with an optical length of cavity nL>5 mm, for example, will provide the frequency displacement Δv of 30 GHz or less depending on requirements. Such a displacement is more than enough for complete spectral displacement of the RBS line from 0 Hz including the Doppler shift considering the aircraft speed and air velocity. It is important that the shift discussed is a one side frequency shift developed by the use of the dual frequency laser 20, which allows directional measurement of wind speed.

The one side frequency shift can be proven mathematically. The frequency of the reference radiation may be denoted as $v_{LO}=v_1$ 22 the frequency of the RBS radiation as $v_{RB}=v_2$ 24 and the Doppler frequency due to wind velocity as $v_D$. Then, we can consider two optical fields incident on the photodetector 42:

$$E_{LO}=A_{LO}e^{i[2\pi v_{LO}t+\varphi_{LO}(t)]}$$
$$E_R=A_{RB}e^{i[2\pi (v_{RB}\pm v_D)t+\varphi_{RB}(t)]}, \quad (1)$$

where $|E_{LO}|^2=A_{LO}^2$ and $|E_{RB}|^2=A_{RB}^2$ are optical powers and $\varphi_{LO}(t)$ and $\varphi_R(t)$ are phases of radiations. The total field at the photodetector 42 is equal to $E_{LO}=E_{RB}$.

Therefore, the photocurrent i(t) generated at the photodetector with responsivity $\mathcal{R}$ is:

$$i(t)=\mathcal{R}\{(A_{RB}e^{i[2\pi(v_{RB}\pm v_D)t+\varphi_{RB}(t)]}+(A_{LO}e^{i[2\pi v_{LO}t+\varphi_{LO}(t)]})\}\times\{(A_{RB}e^{-i[2\pi(v_{RB}\pm v_D)t+\varphi_R(t)]})+(A_{LO}e^{-i[2\pi v_{LO}t+\varphi_{LO}(t)]})\}$$

$$i(t)=\mathcal{R}\{A_{RB}^2+A_{LO}^2+A_{RB}A_{LO}(e^{i[2\pi(v_{RB}\pm v_D-v_{LO})t+\Delta\varphi(t)]}+e^{-i[2\pi(v_{RB}\pm v_D-v_{LO})t+\Delta\varphi(t)]})\}$$

$$i(t)=\mathcal{R}\{A_R^2+A_{LO}^2+2A_{RB}A_{LO}\cos[2\pi(\Delta v\pm v_D)t+\Delta\varphi(t)]\}, \quad (2)$$

where $$\Delta\varphi(t)=\varphi_{RB}(t)-\varphi_{LO}(t)$$
$$\Delta v=v_{RB}-v_{LO}$$

For the dual frequency laser 20, shown in FIG. 2, the value of $\Delta v=v_1-v_2$ is the frequency separation between two longitudinal modes. As was shown above, this value can be very large and it provides for unambiguous measurement of Doppler frequency or wind velocity direction as shown in equation (2) above.

Of course, the RBS spectral width and Doppler shift depend on the wavelength of radiation and both values are considerably smaller for a longer wavelength. However, the intensity of RBS is inversely proportional to the fourth power of wavelength and this is why application of short wavelength lasers is preferable for RBS measurements.

Figure 3:
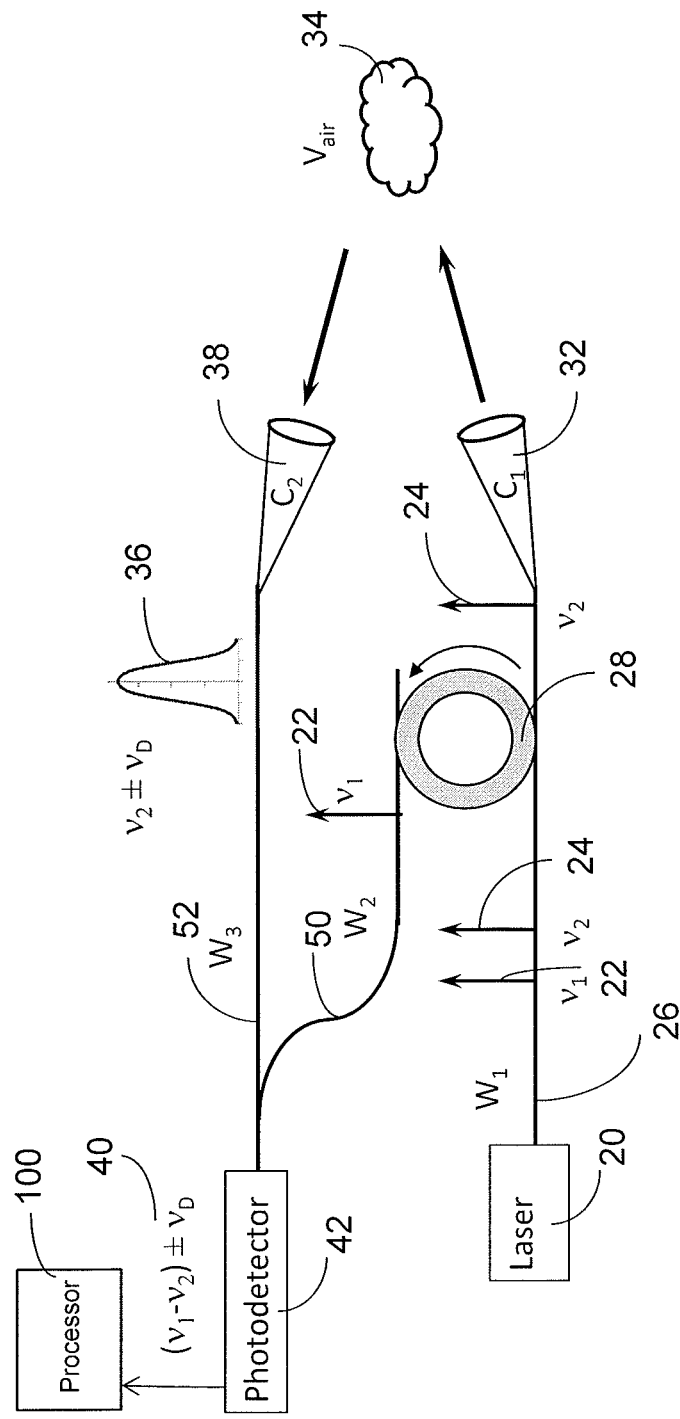
FIG. 3 shows another embodiment of an apparatus for measurement of at least one of air pressure, temperature, and wind velocity in accordance with the present disclosure.

Different embodiments of the apparatus shown in FIG. 2 can be developed. For example, the received scattered radiation 36 may be coupled into a separate waveguide W3 52 shown in FIG. 3, to reduce any possible losses of the received RBS signal 36 as it passes by bandpass filter 28 in the embodiment of FIG. 2. In the embodiment of FIG. 3, the radiation of frequency $v_1$ 22 is coupled by optical microresonator 28, which is a narrow bandpass filter, and redirected into waveguide $W_2$ 50. Then the received RBS signal 36 and the reference $v_1$ 22 are mixed at the photodetector 42.

An output of photodetector 42 in FIG. 3 may be connected to a processor 100 in order to derive the wind velocity including its direction, and also to derive the air temperature and air pressure.

The schematics shown in FIGS. 2 and 3 allow measurement of only one component of wind velocity which is the projection of total velocity on the direction of RBS beam detection. To get more complete data about wind velocity, it is necessary to measure at least three components of velocity along non-collinear directions.

Figure 4:
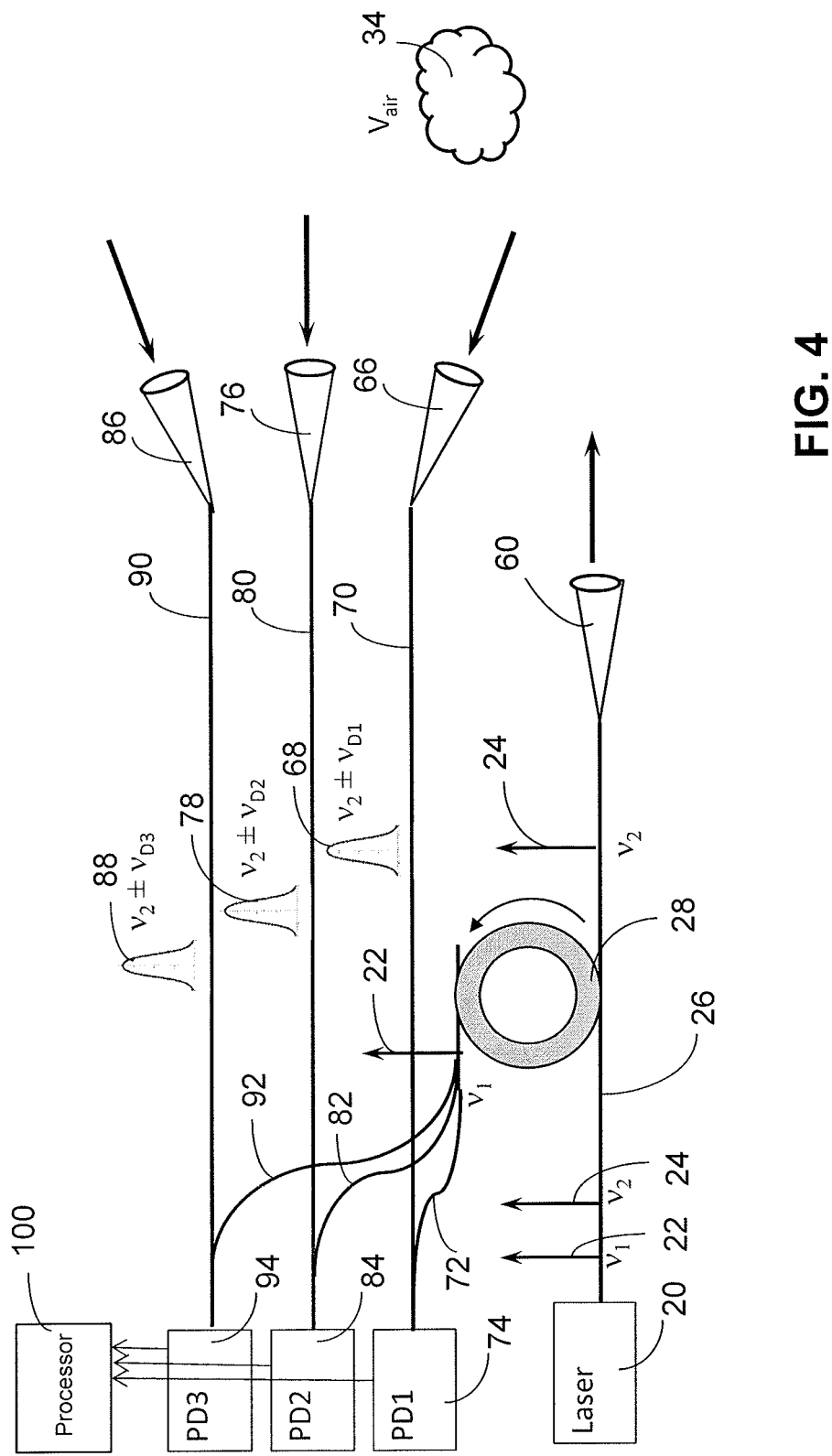
FIG. 4 shows yet another embodiment of an apparatus for measurement of three components of velocity along non-collinear directions in accordance with the present disclosure.

FIG. 4 shows one possible embodiment for measuring at least three components of velocity along non-collinear directions. The radiation of laser 20 with frequencies of $v_1$ 22 and $v_2$ 24 is coupled to waveguide 26. The radiation of frequency $v_1$ 22 is coupled by optical microresonator 28, which is a narrow bandpass filter, and redirected into waveguides 72, 82 and 92. The radiation of frequency $v_2$ 24 is transmitted past the microresonator 28, and outcoupled from waveguide 26 through at least one collimator 60. The radiation of frequency $v_2$ 24 from the at least one collimator 60 is beamed to the air volume $V_{air}$ 34. Then broadband spectral lines of RBS from the air volume 34 of central frequency $v_2$ are received by collimators 66, 76 and 86, which are set or arranged in non-collinear directions. The received broadband spectral lines of RBS have Doppler shifts of $+v_{D1}$ or $-v_{D1}$ 68, $+v_{D2}$ or $-v_{D2}$ 78, and $+v_{D3}$ or $-v_{D3}$ 88, respectively, and are coupled into waveguides 70, 80 and 90, respectively. Then the broadband spectral lines of RBS of central frequency $v_2$ with Doppler shifts $+v_{D1}$ or $-v_{D1}$ 68, $+v_{D2}$ or $-v_{D2}$ 78, and $+v_{D3}$ or $-v_{D3}$ 88 are mixed with reference frequency $v_1$ 22 developing beat frequencies $(v_1-v_2) \pm v_{D1}$, $(v_1-v_2) \pm v_{D2}$, $(v_1-v_2) \pm v_{D3}$, on photodetectors 74, 84 and 94, respectively. By measuring the at least three components of velocity along non-collinear directions, the direction of wind velocity is more completely measured. An output of each of the photodetectors 74, 84 and 94 may be connected to a processor 100 in order to derive the wind velocity and direction of the wind velocity, and also to derive the air temperature and air pressure.

The microresonator 28 in the embodiments shown in FIGS. 2, 3 and 4 may be an optical microresonator, a microring resonator, a plurality of mutually coupled ring resonators, or a plurality of coupled microresonators.

Any laser 20 having a proper cavity design which results in the required longitudinal mode separation can be used. The laser 20 may be a semiconductor laser, a laser diode, a quantum cascade laser, or an optical fiber laser. The progress in semiconductor lasers in the last decade has resulted in development of small-sized high power lasers which can be directly used in integrated optical circuits. Therefore, the application of semiconductor lasers is preferable.

It is not necessary to use a laser having only two frequencies or two modes. A laser having a two or more longitudinal modes can also be used. Moreover, the use of lasers having one powerful longitudinal mode and a few weak modes is preferable. The most powerful mode can be used for air exposure and any adjacent weak mode having 10 or even 100 times lower intensities can be used as for the reference radiation. Laser diodes, quantum cascade lasers and optical fiber lasers can be developed by application of well-known techniques by proper design of periodic structures such as distributed feedback Bragg (DFB) gratings over the active region of lasers or distributed Bragg reflectors (DBR) as one of the laser mirrors. Another narrowband reflector which can be used as a mirror for spectral design of any laser is volume Bragg grating (VBG).

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. An apparatus for measuring pressure, temperature, or wind velocity of a volume of air comprising:
    a laser for transmitting a first frequency and a second frequency;
    a first waveguide coupled to the laser;
    a second waveguide;
    a narrowband filter coupled between the first waveguide and the second waveguide, wherein the narrowband filter is configured to couple the first frequency to the second waveguide; and
    a photodetector coupled to the second waveguide;
    wherein the second frequency is transmitted by the first waveguide to the volume of air;
    wherein scattered light is received on a receive waveguide from the volume of air and coupled to the photodetector;
    wherein the photodetector mixes the first frequency on the second waveguide with the received scattered light on the receive waveguide; and
    wherein the first waveguide and the receive waveguide are different waveguides.

2. The apparatus of claim 1 wherein:
    the second waveguide is the receive waveguide.

3. The apparatus of claim 2 further comprising:
    a first collimator coupled to the first waveguide; and
    a second collimator coupled to the second waveguide.

4. The apparatus of claim 1 wherein the receive waveguide is a different waveguide than the second waveguide.

5. The apparatus of claim 1 wherein:
    the laser has at least two longitudinal modes.

6. The apparatus of claim 1 wherein:
    the laser comprises a semiconductor laser, a laser diode, a quantum cascade laser, or an optical fiber laser.

7. The apparatus of claim 1:
wherein the received scattered light comprises Rayleigh-Brillouin scattering.

8. The apparatus of claim 1:
wherein the received scattered light comprises a Doppler shift due to a wind velocity.

9. The apparatus of claim 1:
wherein the first frequency is $v_{1m}$;
wherein the second frequency is $v_{2m}$; and
wherein $\Delta v = v_{1m} - v_{2m}$ is equal to $c/(2nL)$, where c is a speed of light, n is a refractive index of a cavity material of the laser, and L is a cavity length of the laser.

10. The apparatus of claim 9:
wherein an optical length of the cavity nL is greater than 5 mm, so that $\Delta v = v_{1m} - v_{2m}$ is equal to or less than 30 GHz.

11. The apparatus of claim 1 wherein:
the narrowband filter comprises an optical microresonator, a microring resonator, a plurality of mutually coupled ring resonators, or a plurality of coupling microresonators.

12. The apparatus of claim 1 further comprising:
a processor coupled to the photodetector for deriving an air pressure, an air temperature, or a wind velocity including wind direction from a measured spectrum of the received scattered light.

13. A method of measuring air pressure, temperature, or wind velocity of a volume of air comprising:
transmitting a first frequency from a laser and a second frequency from the laser through a first waveguide;
coupling the first frequency into a second waveguide;
transmitting the second frequency from the first waveguide to the volume of air;
receiving light scattered from the volume of air on a receive waveguide, wherein the receive waveguide is coupled to a photodetector;
mixing in the photodetector the received scattered light on the receive waveguide with the first frequency on the second waveguide;
measuring a spectrum of a beat frequency from the photodetector; and
deriving an air pressure, an air temperature, or a wind velocity including wind direction from the measured spectrum;
wherein the first waveguide and the receive waveguide are different waveguides.

14. The method of claim 13 wherein:
the receive waveguide is the second waveguide.

15. The method of claim 13: wherein the receive waveguide is a different waveguide than the second waveguide.

16. The method of claim 13 wherein:
the laser has at least two longitudinal modes.

17. The method of claim 13 wherein:
the laser comprises a semiconductor laser, a laser diode, a quantum cascade laser, or an optical fiber laser.

18. The method of claim 13:
wherein the received scattered light comprises a Doppler shift due to a wind velocity.

19. The method of claim 13:
wherein the first frequency is $v_{1m}$;
wherein the second frequency is $v_{2m}$; and
wherein $\Delta v = v_{1m} - v_{2m}$ is equal to $c/(2nL)$, where c is a speed of light, n is a refractive index of a cavity material of the laser, and L is a cavity length of the laser.

20. The method of claim 19:
wherein an optical length of the cavity nL is greater than 5 mm, so that $\Delta v = v_{1m} - v_{2m}$ is equal to or less than 30 GHz.

21. The method of claim 13 wherein receiving light scattered from the volume of air comprises:
receiving light scattered from the volume of air from at least three non-collinear directions.

22. The method of claim 13 wherein the received scattered light comprises Rayleigh-Brillouin scattering.

23. An apparatus for measuring pressure, temperature, or wind velocity of a volume of air comprising:
a laser for transmitting a first frequency and a second frequency;
a first waveguide coupled to the laser;
a second waveguide;
a third waveguide;
a fourth waveguide;
a narrowband filter coupled between the first waveguide and the second waveguide, the third waveguide and the fourth waveguide wherein the narrowband filter is configured to redirect the first frequency to the second waveguide, the third waveguide and the fourth waveguide;
at least one collimator coupled to the first waveguide, wherein the second frequency is transmitted by the at least one collimator to the volume of air;
a first, a second, and a third photodetector;
a second collimator coupled to the first photodetector by the second waveguide;
a third collimator coupled to the second photodetector by the third waveguide;
a fourth collimator coupled to the third photodetector by the fourth waveguide;
wherein the second, third and fourth collimators are set in non-collinear directions;
wherein light scattered from the volume of air is received by the second, third and fourth collimators;
wherein the first photodetector mixes the first frequency with the received scattered light from the second collimator;
wherein the second photodetector mixes the first frequency with the received scattered light from the third collimator; and
wherein the third photodetector mixes the first frequency with the received scattered light from the fourth collimator;
wherein the first waveguide, the second waveguide, the third waveguide and the fourth waveguide are each different waveguides.

24. The apparatus of claim 23 further comprising:
a processor;
wherein the first, second and third photodetectors are coupled to the processor for deriving an air pressure, an air temperature, or a wind velocity including wind direction from a measured spectrum of the received scattered light.

25. The apparatus of claim 23:
wherein the received scattered light comprises Rayleigh-Brillouin scattering.

* * * * *